United States Patent [19]

Bruder-Heid et al.

[11] Patent Number: 5,660,994

[45] Date of Patent: Aug. 26, 1997

[54] METHOD OF DETECTING TISSUE-SPECIFIC, INSOLUBLE CYTOSKELETAL PROTEINS

[75] Inventors: Gerda Bruder-Heid; Werner Wilhelm Franke, both of Heidelberg, Germany

[73] Assignee: Progen Biotechnik GmbH, Heidelberg, Germany

[21] Appl. No.: 396,898

[22] Filed: Mar. 1, 1995

Related U.S. Application Data

[63] Continuation of Ser. No. 964,479, Oct. 21, 1992, abandoned, which is a continuation of Ser. No. 547,548, Jul. 19, 1990, abandoned, which is a continuation of Ser. No. 348,536, May 8, 1989, abandoned, which is a continuation-in-part of Ser. No. 180,563, Apr. 12, 1988, abandoned, which is a continuation-in-part of Ser. No. 39,895, Apr. 20, 1987, abandoned.

[30] Foreign Application Priority Data

| Nov. 10, 1986 | [LU] | Luxembourg | 86.652 |
| Nov. 10, 1986 | [LU] | Luxembourg | 86.654 |
| Nov. 10, 1986 | [LU] | Luxembourg | 86.655 |
| May 10, 1988 | [DE] | Germany | 38 15 932.5 |
| Nov. 26, 1988 | [DE] | Germany | 38 02 093.9 |
| Jan. 23, 1989 | [EP] | European Pat. Off. | 8910174.6 |

[51] Int. Cl.$^6$ ................................. G01N 33/574
[52] U.S. Cl. ............... 435/7.23; 435/7.1; 435/7.21; 435/268; 435/172.2; 435/272; 435/330; 435/331; 435/332; 435/344; 436/543; 436/544; 436/548; 436/84; 436/815; 530/350; 530/353; 530/357; 530/387.7; 530/388.85
[58] Field of Search ............... 435/7.21, 7.23, 435/7.1, 28, 172.1, 172.2, 267, 268, 272, 816, 820, 330, 331, 332, 344; 436/543, 544, 547, 548, 84, 815; 530/328, 350, 353, 357, 387.1, 387.7, 388.1, 388.8, 388.85, 808, 842, 851

[56] References Cited

U.S. PATENT DOCUMENTS

| 4,169,138 | 9/1979 | Jonsson. | |
| 4,299,916 | 11/1981 | Litman et al. | 435/6 |
| 4,727,021 | 2/1988 | Cote et al. | 435/172.2 X |
| 4,775,620 | 10/1988 | Cardiff et al. | 436/519 |
| 4,952,507 | 8/1990 | Woodward | 435/240.27 |

FOREIGN PATENT DOCUMENTS

| 0163304 | 5/1985 | European Pat. Off. . |
| 0237252 | 3/1987 | European Pat. Off. . |
| 0267355 | 3/1987 | European Pat. Off. . |
| 0267356 | 3/1987 | European Pat. Off. . |
| WO85/03132 | 7/1985 | WIPO . |

OTHER PUBLICATIONS

Nelson, W., et al., Cancer Res., 44:1600–1603 (1984).
Roop, D. et al., Journ Biol Chem., 259(13):8037–8040 (1984).
Jorcano. J. et al. Journ Mol. Biol., 179:257–281 (1984).
Hintner, H. et al, Journ Clin Invest. 71:1344–1351 (1983).
Tseng, S. et al., Cell 30:361–372 (1982).
Gigi, O. et al., EMBO Journ. L Noll:1429–1437 (1982).
Geisler, N. et al., Cell 30:277–286 (1982).
Von Kosbull, H. et al., Biol Abstr. 74(5), (1982) Abstr #30655.
Woodcock–Mitchell, J. et al. Chem. Abstr. 97 (1982) abstr #211794c.
Weber, K. et al., Biol Abstr., 72(3) (1981), Abstr #17437.
Cremer, M. et al, Biol Abstr. 72(4) (1981), Abstr #22764.
Achstaetter, T., et al., Biol Abstr 83(1) (1987) Abstr. #5344.
Hintner et al., J. Clin. Invest. 71:1344–1351 (1983).
Weber et al., EMBO J. 3:2707–2714 (1984).
Osborn et al., TIBS 11:469–72 (1986).
Albrechtsen et al., J. Neuroimmunol 8:301–309 (1985) Abst. Only.
Getslor et al., "Neurofilament Architecture . . . Triplet Proteins," EMBO J.2:1295–1302 (1983).
Albrechtsen et al., "Glial Fibrillary Acidic . . . Neural Tube Defects," Prenatal Diagnosis 4:405–410 (1984).
Albrechtsen et al., "Quantification of Glial Fibrillary . . . Monoclonal Antibody," J. Neuro Immunol 8:301–309 (1985).
Van Regemorter et al., "Value of Glial Fibrillary Acidic . . . Noural Tube Defects," Clin Chim Acta 165:83–88 (1987).
Chem et al., "Presence of proteoly finally processed Keratins in the culture . . . ," Cancer Research 46:6353–59 (1986).
Mellerick et al., "On the nature of serological tissue polypeptide . . . ," Oncogene 5:1007–1017 (1990).
Dellagi et al., "Human Monoclonal IgM With Autoantibody Activity Against Intermediate Filaments", Proc. Natl. Acad. Sci. USA. vol. 79, Jan. 1982, pp. 446–450.
Osung et al., "Antibody to Intermediate Filaments of the Cytoskeleton in Rheumatoid Arthritis", Ann. Rhea. Dis. (England) vol. 41/1 1982 pp. 69–73 (Abstract).
Senecal et al., "Immunoglobin M Autoantibody to Vimentin Intermediate Filaments", J. Clin. Invest., vol. 69, Mar. 1982, pp. 716–772.
Hansson et al., "Fc–mediated binding of IgG to Vimentin–Type Intermediate Filaments in Vascular Endothelial Cells" Proc. Natl. Acad. Sci. USA vol. 81 (10), May 1984, pp. 3103–3107 (Abstract).
Paulin et al., "In Vitro differentiation of Mouse Teratocarcinoma Cells Monitored by Intermediate Filament Expression", Differentiation, vol. 22 (2), 1982, pp. 90–99 (Abstract).

(List continued on next page.)

*Primary Examiner*—Christine M. Nucker
*Assistant Examiner*—Jeffrey Stucker
*Attorney, Agent, or Firm*—Sughrue, Mion, Zinn, Macpeak & Seas

[57] ABSTRACT

The invention relates to the identification of insoluble cytoskeletal proteins, or fragments thereof, which are characteristic of the origin of the tissue. The invention relates as well to the method for detecting such proteins by breaking down and solubilizing the protein for immunological detection and quantitation. The method allows detection of tissue lesions or other pathological foci and metastases.

19 Claims, No Drawings

OTHER PUBLICATIONS

Bjorklund et al., Tumormarkersystem CEA–TPA, Luthgens M. und Schlegel G., eds. TumorDiagnostick Verlag, Leonberg, S., pp. 14–29 (1987).

Leube et al, Differentiation, 33:69–85 (1986).

Chemical Abstracts, Band 95, 1981, Seite 302, Nr. 37953a, Columbus, Ohio; Nelson et al.: "Properties of a Calcium Ion–activated protoase specific for the intermediate–sized filament protein vimentin in Ehrlich ascites tumor cells", & Eur. J. Biochem. 1981, 116(1), 51–7.

Virtanen et al., J. Cell Sci. 50:45–63 (1981).

Nachr. Chem. Tech. Lab 35 (1987).

J. Immun. Meth., Band 85, 1985, Seiten 401–407, Elsevier Science Publishers B.V. Amsterdam; Hansson et al: "Solid–phase Preparation of Vimentin–type Intermediate Filaments for Immunoassays".

Chemical Abstracts, Band 96, 1982, Seite 498, Nr. 159850f, Columbus, Ohio; Virtanen et al: "Low–ionic Strength Induces Degradation of Vimentin in Cultured Human Fibroblasts", & Biochem. Biophys. Res. Comm. 1982, 105(2), 730–6.

Kurki and Virtanen, J. Immun. Meth., 67:209–223 (2984).

Chemical Abstracts, Band 96, 1982, Seite 458, Nr. 101416c, Columbus, Ohio; Traub et al: "Occurrence in Various Mammalian Cells and Tissues of the Calcium (2+)–activated Protease Specific for the Intermediate–sized filament Proteins Vimentin and Desmin", & Eur. J. Cell. Biol. 1981, 26(1), 61–7.

Kurki et al., Clin. Immunology and Immunopathology 11:379–387 (1978).

Chemical Abstracts, 101:370462 1984.

Chemical Abstracts, 9631704 1982.

METHOD OF DETECTING TISSUE-SPECIFIC, INSOLUBLE CYTOSKELETAL PROTEINS

This is a Continuation of application Ser. No. 07/964,479, filed on Oct. 21, 1992, now abandoned; which in turn is a Continuation of application Ser. No. 07/547,548, filed on Jul. 5, 1990, now abandoned; which in turn is a Continuation of application Ser. No. 07/348,536, filed on May 8, 1989, now abandoned; which in turn is a Continuation-In-Part of application Ser. No. 07/180,563, filed Apr. 12, 1988, now abandoned; which in turn is a Continuation-In-Part of application Ser. No. 07/039,895, filed Apr. 20, 1987, now abandoned.

FIELD OF THE INVENTION

The invention relates to a method of detecting specific proteins within insoluble structures by solubilizing said protein and by immunoassay.

BACKGROUND OF THE INVENTION

Intermediate-sized filaments (IFs) are stable cytoplasmic protein polymers in which the constituent polypeptides interact, intimately and specifically, at various levels of structural hierarchy (for reviews, see Weber & Geisler, In *Cancer Cells. The Transformed Phenotype* (Levine et al., eds.) 1:169–176, Cold Spring Harbor Laboratory Press, Cold Spring Harbor, N.Y. (1984); Quinlan et al., *Cell* 42:411–419 (1985)). At the first level, the α-helical parts of IF polypeptides form two-stranded coiled-coils. These dimers closely associate further into 2 to 3-nm rod-like particles comprising pairs of coiled-coils that represent the fundamental tetrameric subunits of IFs. These tetrameric rod particles then may assemble, via 8 to 12-nm annular and/or 2 to 3-nm long protofilamentous intermediates, into the 8 to 12-nm IFs. These various discrete subunit states have been identified, by biochemical and electron microscope techniques, as the result of limited IF disassembly or as intermediates during reassembly of IFs in vitro (Schlaepfer, *J. Cell Biol.* 74:226–240 (1977); Schlaepfer, *J. Ultrastruct. Res.* 61:149–157 (1977); Ahmadi et al., In *Fibrous Proteins: Scientific, Industrial, and Medical Aspects* (Parry, D., et al., eds.) 2, pp. 161–166 (1980); Renner et al., *J. Mol. Biol.* 149:285–306 (1981); Steinert et al., In *Electron Microscopy of Proteins* (Harris, J. ed.) 1, pp. 125–166, Academic Press, N.Y. (1981); Woods & Gruen; *Aust. J. Biol. Sci.* 34:515–526 (1981); Franke et al., *Biol. Cell* 46:257–268 (1982); Geisler & Weber, *EMBO J.* 1:1649–1656 (1982); Geisler et al., *J. Mol. Biol.* 182:173–177 (1985); Aebi et al., *J. Cell Biol.* 97:1131–1143 (1983); Quinlan et al., *J. Mol. Biol.* 178:365–388 (1984); Quinlan et al., *J. Mol. Biol.* 192:337–349 (1986); Sauk et al., *J. Cell Biol.* 99:1590–1597 (1984); Eichner et al., In *Intermediate Filaments* (Wang, E. et al., eds.), Ann. N.Y. Acad. Sci. 455:381–402 (1985); Ip et al., *J. Mol. Biol.* 183:365–375 (1985); Ip et al., In *Intermediate Filaments* (Wang, et al., eds.), Ann. N.Y. Acad. Sci. 455:185–199 (1985)).

A special requirement for polypeptide chain interaction exists in the cytokeratins, which are obligatory heteropolymers (Lee & Baden, *Nature* (London) 264:377–379 (1976); Steinert et al., *J. Mol. Biol.* 108:547–567 (1976); Milestone, *J. Cell Biol.* 88:317–332 (1981); Hatzfeld & Franke, *J. Cell Biol.* 101:1826–1841 (1985); Eichner et al., *J. Cell Biol.* 102:1767–1777 (1986)) formed by tetramers containing two chains of representatives of either cytokeratin subfamily, i.e., the basic (type II) and acidic (type I) cytokeratins (see, for example, Crewther et al., *Int. J. Biol. Macromol.* 5:267–274 (1983); Franke et al., *Proc. Natl. Acad. Sci. (USA)* 80:7113–7117 (1983); Quinlan et al., *J. Mol. Biol.* 178:365–388 (1984); Sun et al., In *Cancer Cells. The Transformed Phenotype* (Levine et al., eds.), 1, pp. 169–176, Cold Spring Harbor Laboratory Press, Cold Spring Harbor, N.Y. (1984); Woods & Inglis, *Int. J. Biol. Macromol.* 6:277–283 (1984); Fuchs, E. et al., In *Intermediate Filaments* (Wang, E. et al., eds.), Ann. N.Y. Acad Sci. 455:436–450 (1985). It is not yet clear whether the coiled-coil polypeptide dimers are homotypic or heterotypic (Franke et al., *Proc. Natl. Acad. Sci. (USA)* 80:7113–7117 (1983); Gruen & Woods, *Biochem. J.* 209:587–598 (1983); Quinlan et al., *J. Mol. Biol.* 178:365–388 (1984); Parry et al., *Biochem. Biophys. Res. Commun.* 127:1012–1018 (1985); Ward et al., *Biochemistry* 24:4429–4434 (1985)). It is evident, however, that the type I and type II polypeptides present in the subunits are held together, in large part, by strong hydrogen bonds. Increasing concentrations of urea reveal a relatively sharp dissociation curve characteristic of a given cytokeratin combination (Franke et al., *Proc. Natl. Acad. Sci. (USA)* 80:7113–7117 (1983)).

IF proteins are members of a large multigene protein family that share amino acid sequence homologies (Geisler & Weber, *Proc. Natl. Acad. Sci. (USA)* 78:4120–4123 (1998); Geisler & Weber, *EMBO J.* 1:1649–1656 (1982); Quax et al., *Cell* 35:215–223 (1983)). Amino acid sequence data as well as biochemical studies have revealed a common structural three-domain organization for all types of IF proteins: (1) a non-helical head domain variable in length and amino acid sequence; (2) a central highly α-helical rod domain of ~310 amino acids, and (3) a non-helical tail domain of variable length, which, at least in its first part, is not α-helical (Steinert, et al., supra). The rod domain, which contains most of the IF protein sequence homologies, can be subdivided into three distinct coiled-coil domains, designated coils 1a, 1b and 2 (Geisler & Weber, *EMBO J.* 1:1649–1656 (1982); Weber & Geisler, In *Cancer Cells. The Transformed Phenotype* (Levine et al., eds.) 1, pp. 153–159, Cold Spring Harbor Laboratory Press, Cold Spring Harbor, N.Y. (1984)), which are separated by short non-α-helical spacers ("linkers").

On the basis of the relative degree of homology of the rod domain sequences, the IF proteins can be divided into three major classes (Weber & Geisler, supra; Steinert et al., *Cell* 42:411–419 (1985)) that share not more than 30% homology with each other. One group (type III IF proteins) comprises the non-epithelial proteins desmin, vimentin, glial filament protein and the neurofilament proteins NF-L, NF-M and NF-H, exibiting ≥50% sequence homology within this group. The two other groups are the acidic (type I) and the basic (type II) cytokeratins.

Studies involving limited proteolysis of IF subunits indicate that the rod domain represents the structural building block and that isolated rod fragments alone do not assemble into long protofilaments and IFs (Steinert, *J. Mol. Biol.* 123:49–70 (1978); Geisler et al., *Cell* 30:277–286 (1982)). For non-keratinous IF proteins, it has been reported that enzymic removal of the head piece, or parts thereof, results in assembly-incompetent fragments (Traub & Vorgias, *J. Cell. Sci.* 63:43–67 (1983); Kaufmann et al., *J. Mol. Biol.* 185:733–742 (1985); see, however, Lu & Johnson, *Int. J. Biol. Macromol.* 5:347–350 (1983)). Experiments in which epidermal cytokeratins have been treated with chymotrypsin (Sauk et al., *J. Cell-Biol.* 99:1590–1597 (1984)) also suggested that removal of both heads and tails of cytokeratins leads to fragments that have lost their capability to form IF.

From the finding that the shortest IF polypeptide of known sequence, cytokeratin 19, is devoid of a non-α-helical tail region (Bader et al., *EMBO J.* 5:1865–1875 (1986)) but assembles into IFs when combined with type II cytokeratins (Hatzfeld & Franke, *J. Cell Biol.* 101:1826–1841 (1985)), it has been concluded that the head piece but not the tail is essential for IF assembly. This conclusion is in agreement with the result of Kaufmann et al., supra, who found that proteolytic removal of the last 27 amino acids from the tail of desmin leaves a molecule that can still form IF.

More controversial results have been reported on the structure of the rod domain of cytokeratins. Upon tryptic digestion of bovine epidermal cytokeratins, α-helical particles of $M_r$ 42,000 and 108,000 were found that were originally interpreted to be polypeptide trimers (see, for example, Skerrow et al., *J. Biol. Chem.* 248:4820–4826 (1973)) but were then recognized as tetramers (Woods & Gruen, *Aust. J. Biol. Sci.* 34:515–526 (1981); Gruen & Woods, *Biochem. J.* 209:587–598 (1983); Woods, *Biochem. Int.* 7:769–774 (1983)).

More recently, particles containing tryptic fragments from murine epidermal cytokeratin IFs were resolved into two fractions. These fractions were interpreted to be tetramers and dimers by Parry et al. (*Biochem. Biophys. Res. Commun.* 127:1012–1018 (1985)). These authors concluded that the dimeric particle represented heterotypic coiled-coils arranged in parallel and in register. While these data suggest that both type I and type II cytokeratins, at least those of sheep wool and mammalian epidermis, are recovered in the same proteolytically obtained rod fragments, it is not clear whether the association of the complementary cytokeratins is directed by elements located in the rod domain, or whether certain peptides involved in the recognition and alignment of these chains are located outside of the rod domain. For example, it has been discussed that the head and tail domains of the cytokeratins might be responsible for the complementarity of binding and the strong hydrogen bonds formed between type I and type II cytokeratins (Weber & Geisler, supra).

During the development of certain organs, the organization of one-layered polar epithelia changes and transforms into stratified epithelia. At this point, the induction of cytokeratin synthesis (i.e., cytokeratins 3–6 and 9–17) appears to be related to the stratification process. Two of the earliest stratification-related cytokeratin polypeptides are cytokeratin 4, a representative of the type II subfamily, and the type I cytokeratin 13, which are expressed, at least transiently, during the development of all diverse stratified epithelia studied so far, including embryonic epidermis. While these two cytokeratins seem to disappear in later maturation stages of epidermis, they represent the most abundant cytokeratins in several adult non-epidermal stratified epithelia such as oral and lingual mucosa, laryngeal and pharyngeal epithelia, epiglottis, esophagus, exocervix and vagina. See Banks-Schlegel, *J. Cell Biol.* 93:551–559 (1982); Banks-Schlegel, *Cancer Res.* 44:1153–1157 (1984); Fuchs, E., et al., In *Intermediate Filaments* (Wang, E., et al., eds.), Ann. N.Y. Acad. Sci. 455:436–450 (1985); Moll, R., et al., *Cell* 31:11–24 (.1982); Moll et al., *Differentiation* 23:256–269 (1983); Moll R., et al., *Lab. Invest.* 49:599–610 (1983); Nagle, R. B., et al., *Differentiation* 30:130–140 (1985); Ouhayoun, J.-P., et al., *Differentiation* 30:123–129 (1985); Quinlan, R. A. et al., In *Intermediate Filaments* (Wang, E. et al., eds.), Ann. N.Y. Acad. Sci. 455:282–306 (1985).

Corresponding cytokeratin polypeptides abundant in, for example, esophageal epithelium, have been described in several animal species. Cooper, D., et al., *J. Biol. Chem.* 261:4646–4654 (1986); Cooper et al., *Lab. Invest.* 52:243–256 (1985); Doran, T. I., et al., *Cell* 22:17–25 (1980); Franke, W. W., et al., *J. Mol. Biol.* 153:933–959 (1981); Knapp, B., et al., *J. Biol. Chem.* 262:938–945 (1987); Milestone, L. M., *J. Cell. Biol.* 88:317–322 (1981); Schiller, D. L:, et al., *EMBO J.* 1:761–769 (1982). Consequently, the "expression pair" of cytokeratins 4 and 13 has been regarded as the cytoskeletal hallmark for epithelial differentiation of the "esophageal type".

The histodiagnostic detection of intermediate filament proteins with specific antibodies is known. Such antibodies may be used to determine whether a given tumor growth is of epithelial origin. See, for example, Bannasch, P., et al., *Proc. Natl. Acad. Sci (USA)* 77:4948–4952 (1980). Moreover, antibodies may be used to detect intermediate filament proteins in metastases or other tissue lesions for the determination of the tissue of origin of the primary tumor.

The composition of the desmosome plaque has been especially thoroughly investigated, the main proteins of which, desmoglein, plakoglobin and desmoplakins I and II are histodiagnostically typical for epithelia and epithelial tumors as well as for some other tissues such as myocardiac tissue, meninges and meningiomas. The appearance of fragments of these main proteins in body fluids may be used as an indicator for cell lesions or destructive processes in epithelial and meningeal tissue. Thus, it is desirable to be able to detect such proteins in a body fluid.

Histological identification of tumor associated tissue is limited by the accessibility of the tissue, and by the fact that many tissue samples are not identifiable by histological means. Thus, a need exists for diagnostic tests for the detection and characterization of proteins characteristic of cell types from both tissue and body fluids.

SUMMARY OF THE INVENTION

The invention relates to a method for detecting and quantifying insoluble IF proteins characteristic of the origin of the tissue, by breaking down and dissolving the proteins and detecting the presence of the IF proteins with an antibody specific for the alpha-helical middle peace fragments of the protein.

The invention also relates to a method of detecting neural tube defects of a fetus by centrifuging amniotic fluid to give a pellet, homogenizing the pellet to give a pulp, digesting the pulp with a protease to liberate the alpha-helical middle piece fragments, removing the protease or stopping protease activity by adding a protease inhibitor, centrifuging the mixture to give a solution containing soluble alpha-helical middle piece fragments, and detecting the alpha-helical middle piece-derived fragments characteristic of neural tube defects.

The invention relates as well to a method of identifying the origin of tissue within a sample by contacting a test preparation containing purified IF proteins, or their alpha-helical middle piece fragments, or subfragments thereof, with a body fluid containing antibodies to said fragments, and detecting whether the antibodies bind to the fragments.

The invention provides for a quick and easy test for the presence of metastatic tissue in a sample, and allows for the identification of the origin of the metastatic tissue.

DESCRIPTION OF THE PREFERRED EMBODIMENTS

The invention relates to a method for the detection and quantitation of tissue-specific insoluble cytoskeletal protein within a biological sample by breaking down and dissolving the sample to expose the protein, followed by immunological detection and quantitation.

By "test preparation" is intended purified IF proteins or alpha-helical middle piece fragments derived from IF proteins.

By "body fluid" is intended any fluid which may be removed from a human which contains intermediate filament proteins. Such body fluids include, but are not limited to, blood, blood serum, cerebrospinal fluid, urine, amniotic fluid, or puncture fluids obtained from any other source within the body.

The tissue-typical proteins within such insoluble structures may be cytoskeletal proteins. Preferably, they are intermediate filaments (IF) or desmosomal proteins.

The invention makes use of the following recognition of workers in the field of cell biology. Intermediate filament (IF) proteins, which comprise insoluble cellular constituents of the cytoskeleton, are proteins of great cell type specificity and characterized by high stability. Some typical association of particular IF proteins with certain tissue types are presented in Table 1.

TABLE 1

| Tissue | Intermediate Filament Protein |
|---|---|
| muscle | desmin |
| neuronal | neurofilament proteins (NF-L, NF-M, NF-H) |
| mesenchymal | vimentin |
| astrocytic | gliafilament protein (also called "glial fibrillary acidic protein") |
| epithelial | cytokeratins |

The identification of these IF proteins is accomplished by sandwich ELISA for each filament type utilizing antibodies specific for each IF protein.

To identify metastatic tissue, it is necessary to identify the different cell types present in a tissue sample. This is accomplished by homogenizing the tissue sample, then breaking down the homogenate until the alpha-helical middle piece fragments are freed from at least a considerable part of the intermediate filament proteins. The soluble fraction is then sepanated out and the IF protein fragments contained therein are immunologically identified.

A further aspect of the invention relates to a method of determining the extent of metastatic spread of a tumor in an individual. This is accomplished by detecting and quantifying intermediate filament proteins present in a cell homogenate and determining the relative ratios of IF proteins present.

There are a number of different cytokeratins (CK 1–19) whose expression patterns are characteristic of different epithelial tissues. See, for example, Moll, R., et al., Cell 31:11–24 (1982). There are sufficient differences present in the CKs and in the alpha-helical middle pieces of cytokeratin IF proteins to allow their selective detection. Thus, it is preferable to detect and quantitate the relative portions of the identified cytokeratins to determine the identity of the epithelial tissue.

Since metastases usually invade lymphoid tissue first, this method is preferably used on lymphoid tissue. The IF proteins function as markers for the tissue of origin, which is identified as foreign tissue, e.g. breast tissue, in a lymph node.

In order to prevent the excessive breakdown of the alpha-helical middle pieces, which may hinder their identification, the IF proteins are solubilized to the extent of 80 to 100% by weight at a temperature of 0°–40° C. in physiological saline or in buffer solutions. Protease activity may be controlled by removing the enzyme or by the addition of suitable inhibitors. It is advantageous to solubilize the IF proteins only to the extent that the alpha-helical middle pieces remain intact.

The solubilization may be accomplished chemically, e.g., with acids or bases, or physically, e.g., by heating or irradiation. However, the solubilization is preferably performed proteolytically, since the proteolytic hydrolysis of IF proteins can be carefully controlled such that the middle pieces become soluble and, in addition, sufficiently intact to allow identification.

After a sample containing insoluble protein structures which comprises IF proteins is broken down proteolytically, relatively stable alpha-helical middle pieces are obtained which can then be identified and quantitated by immunoassay methods. Soluble alpha-helical middle piece fragments may be immunologically detected and quantified.

Intermediate filament proteins and fragments therefrom may also be present in body fluids in solubilized and in insoluble forms. The soluble forms may be directly determined with immunological methods. In order that the insoluble forms may also be assayed by these serological tests, the proteins contained in the body fluids are solubilized until the alpha-helical middle piece fragments are freed from at least a considerable part of any insoluble cytoskeletal proteins present therein. The soluble fraction is then separated and the alpha-helical middle piece fragments are immunologically identified.

The invention permits the detection and quantitation of IF proteins and fragments therefrom in body fluids almost immediately after removal from the body. Thus, the invention permits the course of pathological or therapeutic treatment, e.g., irradiation or chemotherapy, to be effectively monitored by the removal of only body fluid which reduces the need for tissue biopsies. The detection and quantitation may be effected several times in succession, during the tissue-damaging treatment and/or after it, in order that the course of the tissue-damaging treatment can be monitored.

Free cytoskeletal protein fragments in body fluid, which originate from cell lesions, may cause the production of corresponding antibodies in vivo. See, for example, Iwatsuki, K., et al., J. Invest. Dermatot. 87:179–184 (1986); Grubauer, G., et al., J. Invest. Dermatol. 87:466–471 (1986); Scott, D. L., et al., Ann. Rheum. Dis. 40:267–271 (1981); Hintner, H. et al., J. Clin. Invest. 71:1344–1345 (1983); Kurki, P., et al., Clin. Exp. Res. 8:212–215 (1984);and Hintner, H., et al., J. Invest. Dermatol. 84:108–113 (1985). Thus the fragments and associated cell lesions can be identified by the presence of such antibodies. This is accomplished by a further aspect of the invention which relates to a test preparation derived from the purified IF proteins, or fragments thereof, which may be used to detect the antibodies which may be present in a body fluid. Antibodies specific for each IF protein can be both identified and quantified according to the invention. The positive identification of antibodies specific to certain IF proteins in body fluids gives a high probability of the presence of associated lesions. Thus, the invention provides a second method to allow determination of the extent of metastasis.

The standard proteins or fragments thereof which comprise the test preparation are preferably polypeptides which are identical with or substantially identical with the antigenic portion of the cytoskeletal protein. These polypeptides may be obtained from animal tissues or cultured animal or human cells or may be produced synthetically or by the expression of recombinant DNA in prokaryotes or yeast.

For example, Hanukoglu, I., et al., *Cell* 33:915–924 (1983) disclose cloning cDNA, derived from mRNA present in cultured human epidermal cells, which encodes a cytoskeletal keratin (56 KD) from human epidermis and the corresponding amino acid sequence thereof. See also, Tyner, A. L., et al., *Proc. Natl. Acad. Sci. (USA)* 82:4683–4687 (1985), who disclose the DNA and amino acid sequence corresponding to the gene which encodes a 56-KD type II keratin expressed in human epidermis. Quax, W. et al., *Cell* 35:215–223 (1983), disclose cloning the chromosomal gene which encodes the IF protein vimentin. Glass, C., et al., *J. Cell Biol.* 101:2366–2373 (1985) disclose cloning cDNA, using mRNA from cultured human mesothelial cells, which encodes a human type II mesothelial keratin. Johnson, L. D., et al., *Proc. Natl. Acad. Sci. (USA)* 82:19861990 (1985), disclose cloning and amino acid sequence of a 67-KD human epidermal keratin. Marchuk, D., et al., *Proc. Natl. Acad. Sci: (USA)* 82:1609–1613 (1985), disclose cloning a gene which encodes a 50-KD keratin expressed in human epidermal cells. Myers, M. W., et al., *EMBO J.* 6:1617–1626 (1987), disclose isolation of cDNA and genomic clones for one of the two large subunits of human neurofilament protein, NF-M.

IF proteins from animal sources have also been investigated. For example, Quax, W., et al., *Cell* 43:327–338 (1985), disclose isolation and characterization of the hamster desmin gene and its expression in HeLa cells.

Singer, P. A., et al., *J. Biol. Chem.* 26:538–547 (1986), disclose molecular cloning and characterization of the Endo B cytokeratin expressed in mouse embryos. Oshima, R. G., et at., *Differentiation* 33:61–68 (1986) disclose the cloning and comparison of mouse and human keratin 18. Balcarek, J., et al., *Nucl. Acids Res.* 13:5527–5543 (1985), disclose isolation and cloning of the gene which encodes mouse glial fibrillary acidic protein gene. Lewis, S. A., et al., *J. Cell Biol.* 100:843–850 (1985), disclose isolation and cloning of cDNA which encodes the mouse neurofilament protein NF-L from a mouse brain cDNA library. See also Lewis, S. A., et al., *Mol. Cell. Biol.* 6:1529–1534 (1986).

Cell lines containing the IFs may be any of those known to contain IF proteins. For example, human cytokeratins 8, 18 and 19 may be prepared from cultured MCF-7 cells as described by Achstaetter, T., et al., *Methods Enzymol.* 134:355–371 (1986).

Purified cytoskeletal proteins or fragments thereof may be used to provide standards for quantitation. The alpha-helical rod fragments used as standards in the practice of the invention may be obtained by isolation from any cell lines or tissues which produce IF proteins. The procedure involves (1) purification of the intact polypeptides, (2) reconstitution of purified protofilaments and IFs, (3) limited proteolysis to give alpha-helical rod fragments, and (4) purification of the alpha-helical fragments in the first step. The lysed cells may be extracted with any buffer and detergent which does not solubilize the IF proteins. The residual IF proteins may then be solubilized with, for example, a concentrated solution of urea. The mixture may then be chromatographed, for example, on a DEAE-cellulose column or by reverse phase HPLC.

Reconstitution of purified polypeptides to IFs in the second step may be accomplished, for example, by using the specific purified non-keratinous IF protein or by combining equimolar amounts of type I and type II cytokeratins in solution, followed by dialyzing the polypeptides to low concentration salt buffers. Assembly into protofilaments and IFs can be controlled, for example, by electron microscopy of negatively stained samples according to Hatzfeld, M., et al., *J. Cell Biol.* 101:1826–1841 (1985).

The reconstituted IFs may then be subjected to limited proteolysis in the third step with, for example, trypsin, chymotrypsin or thrombin. The extent of proteolytic digestion may be monitored, for example, by gel electrophoresis to maximizie the proportion of polypeptide fragments in the range $M_r$ 38,000–40,000. The alpha-helical rod fragments may then be isolated in the fourth step by, for example, gel chromatography or reversed phase HPLC.

Immunoassays, such as competitive or sandwich type assays, can be used for the detection of the IF proteins or fragments thereof. (See, e.g., Chard, T., *An Introduction to Radio-Immunoassay and Related Techniques*, T. S. Work and E. Work Eds. North Holland (1978); and David et al., U.S. Pat. No. 4,376,110). In general, monoclonal antibodies directed to alpha-helical rod fragments may be prepared, for example, according to Koehler and Milsrein, *Nature* 256:495–497 (1975). Antibodies against human epidermal keratins (designated AE1, AE2 and AE3) prepared according to Eichner, R., et al., *J. Cell Biol.* 98:1388–1396 (1984) may be used. Monoclonal antibodies capable of distinguishing phosphorylated and nonphosphorylated neurofilaments, the neuron-specific class of IFs are disclosed by Sternberger, L. A., et al., *Proc. Natl. Acad. Sci (USA)* 80:6126–6130 (1983); Lee, V. M.-Y., et al., *J. Neurosci.* 6:850–858 (1986); and Lee, V. M.-Y., et al., *J. Neurosci.* 6:2179–2186 (1986).

For the immunological detection of such IF fragments practically all polyclonal and monoclonal antibodies—including those commercially available—may be used, provided the epitope(s) which react specifically with the proteins under question are recognized. For example, for the most common cytokeratins 8, 18 and 19, the following commercially available antibodies might be used: CAM 5.2 available from Becton Dickinson, Mtn. View, Calif., USA; $K_G8.13$, available from BioMakor, Rehovot, Israel; $K_s$pan 1–8, available from PROGEN, Heidelberg, FRG, specific for cytokeratins 1–8 and deposited at the European Collection of Animal Cell Cultures (ECACC) under accession number 88011901 (see Table 2, below); CK-2, available from Boehringer Mannheim, FRG; $K_s19.2$, available from PROGEN, Heidelberg, FRG and deposited at the ECACC, and given accession number 87111302. $K_s9.2$ is specific for cytokeratin 19 (see Table 3, below).

Other antibodies which may be used in the practice of the invention include $K_s8–17.2$, an antibody specific for cytokeratin 8, which is deposited at the ECACC under accession number 87110601 (see Table 4, below); $K_s18–27IV$ and $K_s18–9B1$, antibodies specific for cytokeratin 18, which are deposited at the ECACC under acession number 8711301 and number 89010505, respectively (see Tables 5 and 6, below) and VIM 384, an antibody specific for vimentin, which is deposited at the ECACC under accession number 87110602 (see Table 7, below), available from PROGEN, Heidelberg, FRG.

TABLE 2

Monoclonal Antibody to Cytokeratins of the Basic Cytokeratin Subfamily (CK 1–8)

| | |
|---|---|
| Antibody: | $K_s$ pan 1-8, produced from hybridoma cell line $K_s$ pan 1-8, deposited under ECACC No. 88011901 on January 15, 1988 |
| Category: | Mouse monoclonal (strain BALB/c), obtained after fusion with myeloma cell line X63-Ag8.653 |
| Immunoglobulin Class: | IgG2a |
| Antigen: | Cytoskeletal proteins from cultured human MCF-7 cells |
| Polypeptide Reacting: | Epitope common to various cytokeratins of the basic (type II) subfamily (CK 1-8) |
| Species Positive: | Human, bovine |
| Structures, Antigen and Tissues Recognized: | All epithelia, including, e.g., epidermis, gingiva, tongue, esophagus, hepatocytes and bile ducts, small intestine, colon, mucosa of vagina and cervix, mammary gland epithelium and myoepithelia, thymic reticular epithelium, hair-forming cells and hair |
| Positive Reactivities on Cultured Cell Lines: | MCF-7, RT-112, Detroit 562, RPMI 2650, HT-29, SCC-12 (all human); BMGE, MDBK (all bovine) |
| Human Tumors Reactive: | All carcinomas tested so far, including basal cell epitheliomas, spinous cell carcinoma of epidermis, squamous cell carcinoma of tongue, esophagus, lung and cervix, adenocarcinoma of lung, colon and cervix, renal cell carcinoma, mammary carcinoma, hepatocellular carcinomas |
| Applications: | Pathology (differential diagnosis of tumors, also between different types of carcinomas), cell typing in production and research |

TABLE 3

Monoclonal Antibody to Cytokeratin 19

| | |
|---|---|
| Antibody: | $K_s$ 19.2, produced from hybridoma cell line $K_s$ 19.2, deposited under ECACC No. 87111302 on November 13, 1987 |
| Category: | Mouse monoclonal (strain BALB/c), obtained from fusion with myeloma cell line NSO/u |
| Immunoglobulin-Class: | IgG2b |
| Antigen: | Cytoskeleton from cultured human MCF-7 cells |
| Polypeptide Reacting: | Exclusively cytokeratin 19 ($M_r$ about 40,000) |
| Species Reactive: | Human, bovine |
| Structures, Antigen and Tissues Recognized: | Reactive only with certain epithelia. Positive epithelia include: intestinal mucosa, bile ducts, pancreatic ducts, stomach mucosa, collecting ducts of kidney, ureter, bladder urothelium, seminal vesicle, prostate gland, mesothelium, oviduct, endometrial epithelium, endocervix, bronchial epithelia, mammary gland (ducts, acini), thymic reticular epithelium, laryngeal and pharyngeal epithelia; glandular epithelia of skin; basal cell layers of several stratified epithelia (e.g., anal epidermis, vagina, exocervix, urethra, esophagus, tongue and oral mucosa, gingiva) Negative epithelia are, e.g., epidermis of most body sites, suprabasal strata of most states of diverse stratified epithelia (e.g., exocervix, vagina, tongue, esophagus), hepatocytes, acinar cells of pancreas, proximal tubules of kidney; testis; all mesenchymal tissue; most kinds of muscle tissue; neural tissues, lens tissue, endothelia and other vascular components |
| Positive Reactivities on Cultured Human Cell Lines: | MCF-7, HT-29, HeLa, RT 112, Detroit 562, RPMI 2650, , SCC-12 |
| Human Tumors Reactive: | Adenocarcinomas of colon, stomach, pancreas, gall bladder, endometrium, cervix, cholangiocarcinoma of liver, renal cell carcinoma, transitional cell carcinoma of bladder, carcinoma of ovary, squamous cell carcinoma of cervix, mesothelioma, squamous cell carcinoma of bronchus and lung, large cell carcinoma of lung, small cell carcinoma of lung (intermediate type), carcinoid tumor of bronchus, carcinoma of breast |
| Application: | As in Table 2 |

References
1. Franke, W.W. et al., Banbury Report 21: Viral Etiology of Cervical Cancer. Cold Spring Harbor Laboratory, page 121 (1986)
2. Moll, R. et al., Cell 31: 11–24 (1982)

TABLE 4

Monoclonal Antibody to Cytokeratin 8

| | |
|---|---|
| Antibody: | $K_s$ 8-17.2, produced from hybridoma cell line $K_s$ 8-17.2, deposited under ECACC No. 87110601 on November 6, 1987 |
| Category: | Mouse monoclonal (strain BALB/c), obtained from fusion with myeloma cell line X63-Ag8.653 |
| Immunoglobulin Class: | IgG1 |
| Antigen: | Cytoskeleton from cultured MCF-7 cells |
| Polypeptide Reacting: | Exclusively cytokeratin 8 ($M_r$ about 52,500) |
| Species Reactive:. | Human, bovine |
| Structures, Antigen and Tissues Recognized: | Positive epithelia include: Liver (hepatocytes, bile duct), glandular epithelia of skin and tongue, all common simple epithelia |
| Positive Reactivities on Cultured Human Cell Lines: | MCF-7, HeLa, A-431 |
| Human Tumors Reactive: | Positive carcinomas include: Hepatocellular carcinoma, adenocarcinoma of colon, lung, breast |
| Application: | As in Table 2 |

TABLE 5

Monoclonal Antibody to Cytokeratin 18

| | |
|---|---|
| Antibody: | $K_s$ 18-27IV, produced from hybridoma cell line $K_s$ 18-27IV, deposited under ECACC No. 87111301 on November 13, 1987 |
| Category: | Mouse monoclonal (strain BALB/c), obtained from fusion with myeloma cell line SP2/OAg14 |
| Immunoglobulin Class: | IgG1 |
| Antigen: | Cytoskeleton from cultured human MCF-7 cells |
| Polypeptide Reacting: | Exclusively cytokeratin 18 ($M_r$ about 45,000) |
| Species Reactive: | Human, bovine |
| Structures, Antigen and Tissues Recognized: | Positive epithelia include: Cytokeratin filaments in simple epithelia and glands, e.g. liver (hepatocytes, bile ducts), intestine, bladder (urothelium); certain cells in the basal cell layers of several stratitied epithelia, (e.g., vagina, tongue) |
| Human Tumors Reactive: | Colon carcinoma, breast carcinoma, adenocarinoma of various organs |
| Positive Reactivities on Cultured Human Cell Lines: | MCF-7, HeLa, A-431, Detroit 562, RT-112, |
| Application: | As in table 2 |

TABLE 6

Monoclonal Antibody to Cytokeratin 18

| | |
|---|---|
| Antibody: | $K_s$ 18-9B1, produced from hybridoma cell line $K_s$ 18-9B1, deposited under ECACC No. 89010505 on January 5, 1989 |
| Category: | Mouse monoclonal (strain BALB/c), obtained from fusion with myeloma cell line X63-Ag8.653 |
| Immunoglobulin Class: | IgG1 |
| Antigen: | Reconstituted cytokeratins 8:18 from bovine (calf) liver |
| Polypeptide Reacting: | Exclusively cytokeratin 18 ($M_r$ about 45,000) |
| Species Reactive: | Human, bovine |
| Structures, Antigen and Tissues Recognized: | Cytokeratin filaments in simple epithelia and glands, e.g. liver (hepatocytes, bile ducts), intestine, bladder (urothelium); certain cells in the basal cell layers of several stratified epithelia, (e.g., vagina, tongue) |
| Human Tumors Reactive: | Colon carcinoma, breast carcinoma, adenocarcinoma of various organs |
| Positive Reactivities on Cultured Human Cell Lines: | MCF-7, HeLa, A-431, Detroit 562, RT-112, |
| Application: | As in table 2 |

TABLE 7

| | Monoclonal Antibody to Vimentin |
|---|---|
| Antibody: | VIM 3B4, produced from hybridoma cell line VIM 3B4, deposited under ECACC No. 87110602 on November 6, 1987 |
| Category: | Mouse monoclonal (strain BALB/c), obtained from fusion with myeloma cell line X63-Ag8.653 |
| Immunoglobulin Class: | IgG2a |
| Antigen: | Vimentin purified from bovine lens |
| Antigen recognized in Species (tested so far): | Human, bovine, rodent (rat, mouse, hamster), chicken, amphibia (Xenopus) |
| Tissue Specificity: | All cells shown to be positive with antisera to vimentin were also positive with this antibody: cells of mesenchymal derivation, including endothelial cells and certain smooth muscle cells of the vascular tract, fibroblasts, connective tissue, all types of blood cells, including thymocytes, interstitial and Sertoli-cells of testis, ovarian follicle cells; detects coexpression of vimentin in combination with other IF proteins |
| Positive Reactivities on Cultured Cell Lines: | RD calls, glioma cells, fibroblasts (SV-80, 3T3), BHK |
| Human Tumors Detected: | All vimentin expressing tumors such as sarcomas (including myosarcomas), lymphomas, melanomas etc. |
| Application: | As in Table 2 |

In order to identify neurofilament proteins, antisera against neurofilament proteins (NF-8 (PROGEN, Heidelberg, FRG)) may be used in the present invention.

In order to identify gliafilament proteins, antisera against gliafilament proteins (guinea pig antiserum GF-100) and monoclonal antibody GF 12.24 (PROGEN, Heidelberg, FRG) may be used in the present invention. Another useful antibody against neurofilament proteins is commercially available from Boehringer Mannheim, FRG.

More or less of the IF proteins actually present may be identified via their α-helical rods and epitope-bearing fragments thereof, depending on the type of tissue, the kind of pre-treatment and the performance of the test. Therefore, under certain circumstances, the actual amount of IF proteins present, i.e., inclusive of IF proteins not natively belonging to the investigated tissue, does not offer a definitive statement as to the state of differentiation and tissue type. A better result is obtained when a ratio is determined based on the identified foreign IF proteins and the identified IF proteins that are typical for the tissue in question. Preferentially, the IF proteins present in the sample tissue are first identified according to their tissue type. Then, the ratio of the detected amount of IF proteins foreign to the tissue type of the sample tissue in question and the detected amount of IF proteins characteristic of the tissue in question is calculated. Next, this ratio is compared with a standard-ratio obtained from a non-pathological sample of the same type of tissue.

Cancer cells may detach from a tumor and preferentially invade lymphoid tissue situated next to the tumor, producing so-called "lymph node metastases". Using the above-described procedures, the present invention can be employed to detect metastatic spread in a lymph node sample. This is accomplished by determining the ratio of the detected amount of IF protein characteristic of the tumor cell type, to the detected amount of IF protein, e.g., vimentin, characteristic of the invaded tissue, e.g., lymphoid tissue.

The following examples are provided for illustrative purposes only and are in no way intended to limit the scope of the present invention.

EXAMPLE 1

Isolation and Purification of Standard α-helical Rods and Epitope-bearing Fragments Thereof The method used herein is demonstrated with cytokeratins. However, this method could be employed with any other IF protein.

To obtain α-helical rods and epitope-bearing fragments thereof equivalent to that obtained from proteolytic digestion of native IF proteins, the individual IF protein monomers were (1) purified, (2) reconstituted to form protofilaments and IF, (3) digested under controlled conditions with a protease, and (4) the resulting α-helical rods and epitope-bearing fragments thereof purified from the digestion mixture.

A. Purification of IF Protein Monomers

Human cytokeratins (e.g., 8, 18 and 19) were prepared from homogenates of cultured human MCF-7 cells, essentially as described by Achstaetter, T. et al., *Meth. Enzymol.* 134:355–371 (1986).

Bovine cytokeratin 8, 18 and 19 (Bader, B. L. et al., *EMBO J.* 5:1865–1875 (1986)) were isolated from bladder urothelial cells by scraping the inner surface of bovine bladders. The thus obtained epithelial cells were homogenized as described by Achstaetter, T. et al., *Meth. Enzymol.* 134:355–371 (1986).

Bovine vimentin was isolated from bovine lens according to Bloemendal et al., *FEBS* (2191) 180:181–184 (1985) and Hatzfeld et al., *J. Mol. Biol.* 197:237–255 (1987).

More specifically, cytoskeletal material was extracted for 2 hours in buffer comprising 9.5M urea, 5.0 mM dithioerythritol, 10 mM Tris-HCl (pH 8.0) (hereinafter "9.5M urea buffer"). The extract obtained as supernatant after centrifugation at 100,000×g was dialyzed against buffer comprising 8.0M urea, 2.5 mM dithioerythritol, 30 mM Tris-HCl (pH 8.0) (hereinafter "8.0M urea buffer"). The resulting material was applied to a DEAE-cellulose column (DE 52/Whatman Chemical Separation Inc., Clifton, N.J., USA) which had been equilibrated with 8.0M urea buffer essentially as described by Hatzfeld, M. and Franke, W. W., *J. Cell Biol.* 101:1826–1841 (1985); Achtstaetter, T. et al., *Meth. Enzmol:* 134,355–371 (1986); Bader, B. L. et al.,

*EMBO J.* 5:1865–1875 (1986); and Quinlan, R. A. et al., In *Intermediate Filaments*, Eds. Wang, E. et al., Vol. 455, Ann. N.Y. Acad. Sci., New York, pp. 282–306 (1985). Bound protein was eluted with a 0 to 100 mM guanidinium-HCl gradient. The polypeptide composition was monitored by SDS-PAGE. Pooled fractions were further purified by reverse phase high-pressure liquid chromatography, using 0.01% (v/v) trifluoric acid (TFA) (Fluka, Buchs, Switzerland) as the aqueous phase (solvent A), 0.07% (v/v) TFA in acetonitrile (chromatographic grade, Merck Darmstadt, FRG.) as the organic phase (solvent B) and a BioRad RP 304 reverse phase column (BioRad Laboratories, Richmond, Calif., USA). The peak fractions containing purified IF protein monomers were collected, the acetonitrile removed by vacuum evaporation, and the fractions lyophilized.

B. Reconstitution of Purified IF Protein Monomers to Form Protofilaments and IF

The resulting purified monomers obtained in step (A) were dissolved in 9.5M urea buffer. Then, in the case of the cytokeratins, equimolar amounts of cytokeratins of type I and type II were mixed at concentrations of approximately 0.5 mg/ml. Protofilaments and IFs were obtained by dialyzing the resulting polypeptide solution to a low salt concentraion using the buffers described by Hatzfeld, M. and Franke, W. W., *J. Cell Biol.* 101:1826–1841 (1985). Assembly into protofilaments and IF proteins was monitored by electron microscopy of negatively stained samples as described by Hatzfeld, M. and Franke, W. W., *J. Cell Biol.* 101:1826–1841 (1985).

C. Preparation of α-helical Rods and Epitope-bearing Fragments Thereof by Proteolytic Digestion of Reconstituted IF Proteins Proteolytic digestion of the reconstituted IF proteins obtained in step (B) was performed with various proteases so as to obtain α-helical rods and epitope-bearing fragments thereof. In a typical preparation, chymotrypsin (EC 3.4.21.1 from bovine pancreas) was used at an enzyme to substrate ratio (weight/weight) of 6.6:1000 for the cytokeratin 8:18 pair, a ratio of 9:1000 for the cytokeratin 8:19 pair and a ratio of 2:1000 for vimentin. Digestion with chymotrypsin was performed in 1.0 mM Tris-HCl (pH 8.0). For each chymotrypsin digestion the digestion time had to be optimized. Proteolytic digestion was monitored by SDS-PAGE analyses of the obtained products and was optimized for the maximal proportions of rod sized polypeptide fragments ($M_r$ about 38,000–43,000). After the appropriate digestion time, the enzyme activity was terminated by the addition of 5.0 mM phenylmethyl-sulfonyl fluoride.

D. Purification of α-helical Rods

The proteolytic fragments, i.e., α-helical rods and epitope-bearing fragments thereof, obtained in step (C) were either separated by chromatography on Sepharose CL-6B or directly applied to a reverse phase column for high pressure liquid chromatography.

More specifically, the proteolytic fragments were separated on a BioRad RP304 reverse phase column using the solvent system described in step (A). For further purification, peak fractions were diluted with solvent A so as to reduce the acetonitrile concentration to about 20% (v/v) and then directly applied to a µBondapak $C_{18}$ reverse phase column (Waters Associates, Milford, Mass.). All of the peak fractions were lyophilized and samples examined by 1- and 2-dimensional gel electrophoresis for the presence of α-helical rods. The purified α-helical rods, some of which were further divided into the two epitope-bearing subfragments thereof, were used as standards for calibration of the method of the present invention and for immunization as described in detail below.

EXAMPLE 2

Production of Appropriate Antibodies

A. Preparation of Monoclonal Antibodies Directed to α-helical Rods and Epitope-bearing Fragment Thereof In order to generate specific monoclonal antibodies, only in vitro reconstituted IFs obtained from purified IF protein monomers were employed. To obtain monoclonal antibodies, 6–8 weeks old female BALB/c mice were immunized with 30–300 µg of cytoskeletal proteins or reconstituted IF proteins per injection. The antigens were suspended in phosphate-buffered saline comprising 10 mM sodium phosphate (pH 7.4),150 mM sodium chloride (hereinafter "PBS") and mixed with complete Freund's adjuvant for the first injection. For all of the subsequent injections, incomplete Freund's adjuvant was used. The animals were injected subcutaneously three times, at intervals of approximately three weeks. An intraperitoneal booster injection of 30–80 µg of antigen protein was given three days before removing spleen cells for cell fusion.

Spleen cells obtained from the resulting immunized mice were fused with mouse myeloma cell lines SP2/OAg14, X63-Ag8.653 and NSO/U (Shulmann, M. et al., *Nature* 276:269–270 (1978); Kearney, I. F. et al., *J. Immunol.* 123:1548–1550 (1979); and Clark, M. and Milstein, C., *Somatic Cell Genetics* 7:657–666 (1981)) at a ratio of 10:1, essentially as described by Koehler, G. and Milstein, C., *Nature* 256:495–497 (1975).

Hybridoma supernatants were tested by:

(A) Cryostat sections of human and bovine snap-frozen tissues essentially as described by Achtstaetter, T. et al., *Differentiation* 31:206–227 (1986);
(B) Immunofluorescence microscopy on cultured cells grown on special slides or cover slips; and
(C) By an ELISA, using the purified IF proteins coated onto microtiter plates.

Positive clones were subcloned twice by limited dilution.

Ig subclasses were determined as described by Ouchterlony, O. et al., In: *Handbook of Experimental Immunology*, Ed. Weir, D. M., vol. 1, Chapter 19, Blackwell Scientific Publications, Oxford, pp. 1–19 (1978). Using the above procedures, the hybridomas described in Tables 2–7 were obtained and characterized.

B. Conjugation of Detector-Antibodies to Peroxidase

Antibodies employed as detector-antibodies were coupled to peroxidase using the procedures described by Tijssen, B. In: Laboratory Techniques in Biochemistry and Molecular Biology, Vol. 15: Practice and Theory of Enzyme Immunoassays, Ed. Burdon, R. H., Elsevier Amsterdam, New York, Oxford, page 238; 4th printing (1987).

More specifically, 5.0 mg of peroxidase were dissolved in 0.5 ml of 100 mM sodium bicarbonate buffer (pH 9.2) and prepared for coupling by oxidizing the enzyme with 0.5 ml of 10 mM $NaIO_4$ for 2 hours at room temperature, in the dark, Then, 10 mg of the desired detector-antibody, dissolved in 2.0 ml of the above-described sodium bicarbonate buffer, and 0.5 g of dry Sephadex G-25 (Pharmacia, Freiburg, FRG), were added and incubated in the dark for another 3 hours, at room temperature. The resulting conjugate was eluted from the Sephadex material with the above-described sodium bicarbonate buffer, mixed with a 1/20 volume of freshly prepared $NaBH_4$ (5.0 mg/ml in 0.1 mM NaOH), and after 30 minutes, mixed with a ⅟₁₀ volume of the freshly prepared NaBH₄ solution, followed by 1 hour incubation at 4° C. The resulting conjugate was dialyzed against PBS, concentrated under vacuum to 0.5 ml and fractionated on a Sephadex G-200 (Pharmacia, Freiburg, FRG) column (1.0×50 cm). The fractions (0.5 ml) were tested for immunological and enzymatic activities and fractions containing both, high enzyme and immune activity, were pooled.

EXAMPLE 3

Selection of Appropriate Antibodies

The resulting antibodies of Example 2 were tested for immune reactivity with IF proteins and the α-helical rods and epitope-bearing fragments thereof obtained as described in Example 1, using the following analytical methods:

A. Immuno-blot (reaction with denatured antigen)

Purified IF fragment proteins (e.g., α-helical rods of cytokeratin 8:18, cytokeratin 8:19, and vimentin) and epitope-bearing fragments thereof from sample tissues (e.g., lymph nodes, liver) were electrophoretically separated on SDS-PAGE before and after proteolytic digestion with chymotrypsin as described in Example 4 (see below). The resulting proteins were transferred electrophoretically onto nitrocellulose paper and incubated with the antibodies in question. An immune reaction was detected with labeled protein A or labeled antibodies directed against mouse immunoglobulins. Antibodies Were selected which reacted positively with the a-helical rods ($M_r$ about 38,000–43,000; $M_r$ about 20,000–22,000 in the case of basic cytokeratins).

B. Dot-blot (reaction with native or renatured antigen)

Approximately 2.0 µg of purified reconstituted IF protein which had been solubilized in 50 µl of 50 mM Na₂HPO₄ buffer, (pH 7.4), or 50 µl of the supernatant fraction of homogenized sample tissues after digestion with chymotrypsin as described in Example 4, were directly absorbed onto nitrocellulose paper (e.g., using the SCR 96 minifold I dot-blot apparatus from Schleicher and Schuell, Dassel, FRG) and incubated with the specific antibodies in question. An immune reaction was detected with labeled protein A or labeled antibodies directed against mouse immunoglobulins. Antibodies were selected which reacted positively.

C. ELISA (reaction with native or renatured antigen)

In a 96-well microtiter plate, 500 ng of purified reconstituted IF protein, dissolved in 100 µl of 50 mM NaHCO₃ buffer (pH 9.6) or 2.0 µg of the supernatant fraction obtained after digestion with chymotrypsin as described in Example 4 were dissolved in 100 µl of the same buffer and were coated per well. Bound protein was incubated with the specific antibodies in question. An immune reaction was detected with labeled protein A or labeled antibodies directed against mouse immunoglobulins. Antibodies were selected which reacted positively with the α-helical rods ($M_r$ about 38,000–43,000; $M_r$ about 20,000–22,000 in the case of basic cytokeratins).

D. Immunofluorescence Microscopy

Immunofluorescence microscopy was carried out as described, e.g., by Ciocca, D. R. and Bjercke, R. J., *Meth. Enzymol.* 121:562–579 (1986).

Examples of antibodies which were found to positively react in all of the above four analytical methods were $K_s19.2$; $K_s18-27IV$; $K_s18-9B1$; $K_s8-17.2$; $K_span 1-8$; and VIM 3B4.

EXAMPLE 4

Identification and Determination of Metastases in Lymphoid Tissue

A. Solubilization of IF Proteins

Lymph node tissue was homogenized in a threefold volume (in relation to the moist weight of the lymph node) of PBS with a knife homogenizer (Polytron homogenizer, Kinematica, Lucerne, Switzerland) to give a homogenate with a pulpy consistency. Then, the homogenate was digested with chymotrypsin.

The chymotrypsin employed was previously coupled to a matrix of CNBr-activated Sepharose 4B (Pharmacia, Freiburg, FRG). More specifically, 1.0 g of CNBr-activated Sepharose 4B was swollen for 15 minutes in 1.0 mM HCl (resulting in a gel volume of approximately 3.5 ml) and washed with a final volume of 200 ml 1.0 mM HCl. After removal of the HCl, the matrix material was rapidly washed with 5.0 ml of coupling buffer comprising 0.5M NaCl, 0.1M NaHCO₃ (pH 8.0) (hereinafter "coupling buffer"). Then, under continous agitation for 2 hours, 10 mg of chymotrypsin (EC 3.4.21.1 from bovine pancreas), dissolved in 5.0 ml of coupling buffer, was incubated with the matrix material. Thereafter, the remaining active groups were blocked with 5.0 ml of 0.2M glycine buffer (pH 8.0) for 2 hours. Then, the gel was washed with an excess of coupling buffer (approximately 50 ml) and 10 ml of 0.1M sodium acetate buffer (pH 4.0). Under these conditions, approximately 60% of the added chymotrypsin was coupled, i.e., the Sepharose 4B gel contained 1.7 mg of coupled chymotrypsin per 1.0 ml. To facilitate handling, the gel was diluted twice in PBS (the final chymotrypsin concentration was 0.85 mg/ml). Chymotrypsin was then added to the tissue pulp at a ratio of 1:1000 (based on the moist weight of the tissue). The mixture was incubated at 30° C. (preferably in a unit heater, optionally in a water bath). Digestion was terminated after 30 minutes by immersing the homogenate into an ice bath. The homogenate was centrifuged for 30 minutes at 10,000×g and the supernatant was immediately removed. Note, the coupled chymotrypsin remained in the pellet. Under these conditions, 80 to 95% by weight of the α-helical rods and epitope-bearing fragments thereof were freed from the IF proteins in a still-identifiable state, and some intact IF proteins were also in a soluble state.

B. Detection and Quantitation of Vimentin

The presence of vimentin in the supernatant fraction obtained in step (A) was immunologically determined using a sandwich ELISA using the procedure essentially as described in Example 5 (see below). More specifically, a first antibody, i.e., GP-8 (guinea pig antiserum specific for vimentin), was employed as the capture-antibody directed against a first epitope of the α-helical rod of vimentin, and a second monoclonal antibody, i.e., VIM 384, was employed as the detector-antibody directed against a second epitope of the α-helical rod of vimentin which is independent of and different from the first epitope. Antibody VIM 384 had previously been coupled with peroxidase as described in Example 2.

More specifically, the capture-antibody, dissolved in 50 mM NaHCO₃ (pH 9.6), was coated onto wells of a microtiter plate at a concentration of 10 µg/ml (150 µl/well). In order to obtain a standard curve, purified vimentin α-helical rods and epitope-bearing fragments thereof, dissolved in 150 mM NaCl, 1 mM Na₂HPO₄ (pH 7.4), 0.05% (v/v) Tween 20, were used in concentrations ranging from 10 ng/ml to 500 ng/ml.

As the detector-antibody peroxidase-conjugated VIM 384 was diluted to a final concentration of 0.5 µg/ml in buffer comprising 150 mM NaCl, 10 mM Na$_2$HPO$_4$ (pH 7.4), 1.0% (w/v) bovine serum albumin, 0.05% (v/v) Tween 20 and 150 µl of such were added per well.

For the determination of the amount of vimentin in the sample tissue, the supernatant fraction was diluted in the range of 1:100 to 1:500 with 150 mM NaCl, 10 mM Na$_2$HPO$_4$ (pH 7.4), 0.05% (v/v) Tween 20.

As a substrate, o-phenylenediamine or 2,2-azino-bis (3-ethylbenzthiazolinesulfonate) was used. The enzyme activity was then plotted against the concentration of standard vimentin α-helical rods and epitope-bearing fragments thereof prepared from reconstituted IF proteins to give a standard curve from which the unknown amount of vimentin present in the supernatant fraction was interpolated.

Further determinations were based on this vimentin value as a reference point for determining the ratio with values for other IF proteins.

C. Detection and Quantitation of Cytokeratins

The presence of cytokeratins in the supernatant was immunologically detected using a sandwich ELISA using the procedures essentially as described in Example 5 (see below). More specifically, a first monoclonal antibody, i.e., K$_s$pan 1–8, was employed as the capture-antibody directed against a first epitope common to the α-helical rods of various cytokeratins. This antibody, dissolved in 50 mM NaHCO$_3$ (pH 9.6), was employed at a concentration of 20 µg/ml for the coating of the wells of the microtiter plates (150 µl per well). To obtain a standard curve, the purified cytokeratin 8:18 pair and 8:19 pair α-helical rods and fragments therof, dissolved in 150 mM NaCl, 10 mM Na$_2$HPO$_4$ (pH 7.4), 0.05% (v/v) Tween 20, were used in concentrations ranging from 5.0 ng/ml to 500 ng/ml.

As the detector-antibodies, peroxidase-conjugated antibodies K$_s$18–27IV and K$_s$18–9B1 (for the detection of cytokeratin 18), K$_s$19.2 (for the detection of cytokeratin 19), and K$_s$8–17.2 (for the detection of cytokeratin 8), were used. The detector-antibodies were diluted to a final concentration of 0.5 µg/ml in buffer comprising 150 mM NaCl, 10 mM Na$_2$HPO$_4$ (pH 7.4), 1.0% (w/v) bovine serum albumin, 0.05% (v/v) Tween 20 and 150 µl of such were added per well.

For the determination of the amount of cytokeratin in the sample tissue, the supernatant fraction was diluted 1:100 with buffer comprising 150 mM NaCl, 10 mM Na$_2$HPO$_4$ (pH 7.4), 0.05% (v/v) Tween 20.

As a substrate, o-phenylenediamine or 2,2-azino-bis (3-ethylbenzthiazolinesulfonate) was used. The enzyme activity was then plotted against the concentration of standard to give a standard curve from which the unknown amount of cytokeratins present in the supernatant fraction was interpolated.

The extent of Carcinoma metastasis in the sample tissue was expressed by the ratio of the determined amount of cytokeratin in the supernatant fraction to the determined amount of vimentin in the supernatant fraction.

D. More Precise Determination of a Breast Tumor-Metastases

The progesterone and estrogen hormone receptor content of primary tumor or metastatic tissue may be related to the quantitation of the α-helical cytokeratin content according to Example 4, paragraph (C). The hormone receptor contents may be measured in nuclear and cytoplasmic fractions after homogenization, e.g., according to King, W. J., et al., *Nature* 307:745–747 (1984); Derosa, C., et al., Immunocytochemical Detection of Estrogen Receptor in Breast Cancer Using ABBOTT ER-ICA Kit, Symposium on Estrogen Receptor Determination With Monoclonal Antibodies, Monte Carlo (1984); and Jensen, E. V., Immunochemical Detection and Measurement of Estrogen Receptors, in *Praetherapeutische Tumortestung*, Jonat, W., et al. (eds.), Zuckschwerdt München-Bern-Wien.

The quantitation of hormonal receptors allows adjustment of the amount or type of chemotherapy which should be used. The ratio of hormone receptor to cytokeratin is more relevant in this respect than its ratio to total tissue protein.

EXAMPLE 5

Identification of Metastases in Iliac Crest Biopsies

In this example, the extent of metastases with iliac crest biopsies was determined according to Example 4.

EXAMPLE 6

Identification of Metastases in Sternum Biopsy Specimens

In this example, the extent of metastases within sternum biopsy specimens was determined according to Example 4.

EXAMPLE 7

Quantitative Determination of Cytokeratin 8:18 and 8:19 in Body Fluids

A. Coating of Microtiter Plates

Each well of a 96-well microtiter plate was coated with 2.0 µg of antibody K$_s$pan 1–8 antibody dissolved in 100–150 µl of 50 mM NaHCO$_3$ (pH 9.6). The plate was covered and incubated overnight at 4° C.

B. Washing and Blocking Procedures

Excess antibody was withdrawn by suction. The plate was washed three times, each time with 200 µl of washing buffer comprising 150 mM NaCl, 10 mM Na$_2$HPO$_4$ (pH 7.4), 0.05% (v/v) Tween 20 per well, which was removed by turning the plate upside down. The remaining moisture was removed by tapping the plate slightly onto several layers of absorbing paper. Then, each well of the plate received 200 µl of blocking solution comprising 150 mM NaCl, 10 mM Na$_2$HPO$_4$ (pH 7.4), 0.05% (v/v) Tween 20, 1.0% (w/v) bovine serum albumin, 5.0% (w/v) sucrose and was incubated at room temperature for at least 1 hour; upon longer storage of the plate, 0.01% (w/v) Thimerosal was added.

C. Application of Standard or Body Fluid Samples

Standard cytokeratin 8:18 and 8:19 α-helical rods and epitope-bearing fragments thereof, obtained as described above in Example 1, were dissolved in control serum ("Monitrol" from Merz and Dade, or "Kontrollogen L" or "LU" from Behringwerke, Marburg, FRG) at concentrations ranging from 5.0 ng/ml to 500 ng/ml. The control serum had to be diluted previously with washing buffer in the range of 1:10 to 1:100, depending on the detector-antibody used thereafter. Each well receiving 100 µl of the standard α-helical rods and epitope-bearing fragments thereof solution or body fluid sample, was incubated at room temperature for 90 minutes and washed 4 times as described above with washing buffer.

D. Application of Detector-Antibody

As the detector-antibody, the peroxidase conjugate of either:

(i) antibody K$_s$19.2 (directed against the α-helical rod and epitope-bearing fragments thereof of cytokeratin 19),
(ii) antibody K$_s$18–27IV (directed against the α-helical rod and epitope-bearing fragments thereof of cytokeratin 18), (iii) antibody $K_s18-9B1$ (directed against the α-helical rod and epitope-bearing fragments thereof of cytokeratin 18), or (iv) antibody $K_s8-17.2$ (directed against the α-helical rod and epitope-bearing fragments thereof of cytokeratin 8), was diluted in buffer comprising 150 mM NaCl, 10 mM $Na_2HPO_4$ (pH 7.4) 1.0% (w/v) bovine serum albumin, to an optimal concentration ranging from 0.2 to 0.5 μg/ml and added to respective microtiter plates. Each well of the plates received 100 μl and was incubated at room temperature for 60 minutes. Then, the plates were washed twice as described above with washing buffer and four times with tap water.

E. Substrate Reaction

For each microtiter plate, a substrate solution comprising 10 mg of o-phenylenediamine (or one substrate tablet from Sigma, Munich, FRG) and 10 ml of a 30 % (v/v) solution of $H_2O_2$ dissolved in 10 ml of 0.1M potassium phosphate buffer (pH 6.0) or 0.0347M citric acid, 0.0667M disodium hydrogenphosphate (pH 5.0), was prepared. With the latter buffer, higher absorption values were obtained. Each well of the plates received 100 μl of substrate solution which had been equilibrated at room temperature. The plates were covered, e.g., with aluminum foil, to protect the reaction from light and incubated until the color intensity was satisfactorily developed (approximately after 15 to 30 minutes).

F. Terminating the Enzyme Reaction

The reaction was terminated by the addition of 50 μl of 2.0M $H_2SO_4$. For quantitative determinations, the standard and body fluid sample had to be terminated after identical incubation times.

G. Reading of Results

The microtiter plates were read at 492 nm wavelength with an appropriate photometer, e.g., an ELISA scanner.

While this invention has been described in detail and with reference to specific embodiments thereof, it will be apparent to one skilled in the art that various changes and modifications could be made therein without departing from the spirit and scope thereof.

EXAMPLE 8

Early Diagnosis of Fetal Neural Tube Defects Suspected During Pregnancy 10 ml of amniotic puncture fluid was centrifuged and the sediment homogenized to a pulpy consistency in a three-fold volume (in relation to the moist weight) of a phosphate-buffered saline solution (10 mM sodium phosphate, pH 7.4; 50 mM sodium chloride) with a knife homogenizer. Chymotrypsin was added to the homogenate at a ratio of 1:1000 (based on the moist weight of the tissue). After incubation at 30° C. in a water bath for 30 minutes, the enzymatic activity was inhibited by the addition of 5 mM 2-nitro-4-carboxyphenyl-N, N-diphenylcarbamate (NCDC). The homogenate was then centrifuged for 30 minutes at $10^4 \times g$.

The supernatant contains 80 to 95% by weight of the α-helical middle pieces which are freed from the IF proteins of the homogenate and in a still-identifiable state.

The two centrifuged supernatants are separately tested immunologically for neurofilament and gliafilament protein content by sandwich ELISA. A first monoclonal antibody (NF-8 or GL-8), the so-called catcher antibody, which is directed against a first epitope of the m-helical middle piece of the filament proteins, is used for each of the two filament types. In addition, a second monoclonal antibody (NF-100 or GL-100), the so-called detector antibody, which is directed against a second epitope of the alpha-helical middle piece of the associated filament, is used in each instance. The second epitope is independent of and different from the first epitope.

Detector-antibodies NF-100 and GL-100 were coupled with peroxidase. The α-helical middle piece fragments were quantitated by the enzymatic activity of the peroxidase.

Standardization was accomplished as described in Example 7.

The occurence of glial filament or neurofilament fragments in amniotic fluid specimens is indicative of neural tube defects. This test furnishes a considerably more reliable and rapid prenatal diagnostic test than the known methods previously used.

EXAMPLES 9 TO 11

Like Example 7, whereby, however catcher antibodies are used which recognize the individual cytokeratins in combination. For example, the combination C-501 and C-504 recognizes cytokeratin X, combination C-501 and C-503 recognizes cytokeratin (X+1).

EXAMPLES 12 TO 14

Like Example 7, however, with the difference that combinations of different monoclonal antibodies are used as detector antibodies.

EXAMPLES 15 TO 25

Like Examples 4 to 14, with the single difference that the peptides used for the standardization are identical with the antigen from the α-helical middle piece and are obtained by genetic engineering starting from cDNA sequence data as source for certain constructs and deletion constructs.

EXAMPLE 26

Identification and Determination of Lesions in the Epithelial Tissue by Reaction with the Patient's Antibodies The antibodies against cytokeratins in 1 ml serum of patient blood are immunologically determined by ELISA. For this, a microtiter plate is used which is coated in different fields with purified different cytokeratins (CK 1 to 19) or fragments prepared therefrom or from other IF proteins, like in Examples 1 and 15 to 25. A portion of the body fluid is contacted with each field, the mixture incubated for an appropriate length of time, then the preparation is washed to remove unbound antibody.

The antibodies from the patient blood bound by the immobilized proteins or their alpha-helical middle pieces are identified immunologically with antibodies against IgM or IgG which are detectably labeled with peroxidase.

Purified specific IgG or IgM antibodies from human blood is used for standardization.

EXAMPLES 27 AND 28

Like Example 26, with the single difference that instead of patient blood serum, urine (Example 27) or synovial puncture fluid (Example 28) is used.

What is claimed is:

1. A method for identifying the cellular origin of non-secreted intermediate filament protein material in a tissue sample or body fluid, comprising the steps of:

(a) solubilizing insoluble non-secreted intermediate filament proteins present in said tissue sample or body fluid so as to obtain solubilized α-helical middle pieces of non-secreted intermediate filament proteins, said solubilized α-helical middle pieces of non-secreted intermediate filament proteins being characteristic of the cellular origin of non-secreted intermediate filament protein material in said tissue sample or body fluid, wherein said solubilizing of said insoluble non-secreted intermediate filament proteins is accomplished by homogenizing said sample, proteolytically breaking down said homogenized sample, and separating said solubilized α-helical middle pieces from said insoluble non-secreted intermediate filament proteins by centrifugation, (b) contacting the resulting separated solubilized α-helical middle pieces of non-secreted intermediate filament proteins with an antibody that is specific for α-helical middle pieces of non-secreted intermediate filament proteins of particular cell types, wherein said antibody is selected from the group consisting of:

K,8–17.2, which is used for the identification of α-helical middle pieces or epitope-bearing fragments thereof which contain at least one monomer of cytokeratin 8;

K,18–27IV, which is used for identification of α-helical middle pieces or epitope-bearing fragments thereof which contain at least one monomer of cytokeratin 18;

K,8–9B1, which is used for identification of α-helical middle pieces or epitope-bearing fragments thereof which contain at least one monomer of cytokeratin 18;

K,8–19.2, which is used for identification of α-helical middle pieces or epitope-bearing fragments thereof which contain at least one monomer of cytokeratin 19;

K,pan 1–8, which is used for identification of α-helical middle pieces or epitope-bearing fragments thereof which contain at least one monomer of cytokeratin 1 to 8; and VIM 3B4, which is used for identification of α-helical middle pieces or epitope-bearing fragments thereof which contain at least one monomer of vimentin; and (c) detecting whether said antibody has bound to the resulting separated solubilized α-helical middle pieces obtained in step (b), wherein the binding of said antibody to said separated solubilized α-helical middle pieces identifies the cellular original of said non-secreted intermediate filament protein material.

2. The method of claim 1, wherein said antibody is detectably labeled.

3. The method of claim 2, wherein said detectable label is peroxidase.

4. The method of claim 1, wherein said intermediate filament proteins are selected from the group consisting of vimentin and cytokeratins.

5. The method of claim 1, wherein said proteolytic breaking down is accomplished by the addition of chymotrypsin.

6. The method of claim 1, wherein in step (c) said alpha-helical middle pieces are determined quantitatively using a purified alpha-helical middle pieces standard.

7. A method of detecting neural tube defects of a fetus comprising the steps of:

(a) centrifuging amniotic fluid to give a pellet;

(b) homogenizing the pellet obtained in step (a) to give a pulp, (c) digesting the pulp obtained in step (b) with a protease to liberate α-helical middle pieces of non-secreted intermediate filament proteins, (d) inhibiting or removing the proteases, (e) centrifuging the mixture obtained in step (d) to give a solution containing α-helical middle pieces of non-secreted intermediate filament proteins.

(f) detecting the presence of α-helical middle pieces characteristic of neural tube defects in at least one of the solution step (e) and the supernatant liquid of the centrifugation of step (a) by reacting with an antibody that is specific for the α-helical middle pieces of neural cells characteristic of neural tube defects, wherein the binding of said antibody to said α-helical middle pieces is indicative of neural tube defects, and wherein said antibody is selected from the group consisting of:

K,8–17.2, which is used for the identification of α-helical middle pieces or epitope-bearing fragments thereof which contain at least one monomer of cytokeratin 8;

K,18–27IV, which is used for identification of α-helical middle pieces or epitope-bearing fragments thereof which contain at least one monomer of cytokeratin 18;

K,8–9B1, which is used for identification of α-helical middle pieces or epitope-bearing fragments thereof which contain at least one monomer of cytokeratin 18;

K,8–19.2, which is used for identification of α-helical middle pieces or epitope-bearing fragments thereof which contain at least one monomer of cytokeratin 19;

K,pan 1–8, which is used for identification of α-helical middle pieces or epitope-bearing fragments thereof which contain at least one monomer of cytokeratin 1 to 8; and VIM 3B4, which is used for identification of α-helical middle pieces or epitope-bearing fragments thereof which contain at least one monomer of vimentin.

8. The method of claim 7, wherein said pellet is homogenized in the presence of phosphate-buffered saline with a knife homogenizer.

9. The method of claim 7, wherein said protease is chymotrypsin.

10. The method of claim 7, wherein said protease is inhibited with 2-nitro-4-carboxyphenyl-N,N-diphenylcarbamate or removed from the soluble fraction.

11. A method for identifying the cellular original of tumor cells in a tissue sample or body fluid, comprising the steps of:

(a) homogenizing said tissue sample or body fluid;

(b) proteolytically breaking down the protein in the homogenate until soluble α-helical middle pieces are freed from at least a substantial part of the non-secreted intermediate filament proteins to give solubilized α-helical middle pieces and separating said solubilized α-helical middle pieces by centrifugation, said solubilized α-helical middle pieces of non-secreted intermediate filament proteins being characteristic of the cellular origin of said tumor cells;

(c) contacting the resulting separated solubilized α-helical middle pieces of non-secreted intermediate filament proteins with an antibody that is specific for α-helical middle pieces of non-secreted intermediate filament proteins that are characteristic of particular cells, wherein said antibody is selected from the group consisting of:

K,8–17.2, which is used for the identification of α-helical middle pieces or epitope-bearing fragments thereof which contain at least one monomer of cytokeratin 8;

K,18–27IV, which is used for identification of α-helical middle pieces or epitope-bearing fragments thereof which contain at least one monomer of cytokeratin 18;

K,8–9B1, which is used for identification of α-helical middle pieces or epitope-bearing fragments thereof which contain at least one monomer of cytokeratin 18;

K,8–19.2, which is used for identification of α-helical middle pieces or epitope-bearing fragments thereof which contain at least one monomer of cytokeratin 19;

K,pan 1–8, which is used for identification of α-helical middle pieces or epitope-bearing fragments thereof which contain at least one monomer of cytokeratin 1 to 8; and VIM 3B4, which is used for identification of α-helical middle pieces or epitope-bearing fragments thereof which contain at least one monomer of vimentin; and (d) detecting whether the antibody has bound to said separated solubilized α-helical middle pieces, the binding of said antibody to said separated solubilized α-helical middle pieces identifying the cellular origin of said non-secreted intermediate filament proteins, and thus the cellular origin of said tumor cells.

12. The method of claim 11, wherein said tissue sample is selected from the group consisting of lymph node, bone marrow and epithelial tissue.

13. A method for identifying the cellular origin of tumor cells in a tissue sample or body fluid, comprising the steps of:

(a) centrifuging a tissue sample or body sample fluid containing soluble non-secreted intermediate filament proteins so as to separate α-helical middle pieces of non-secreted intermediate filament proteins that are characteristic of the cellular origin of tumor cells in said tissue sample or body fluid, (b) contacting the resulting separated soluble α-helical middle pieces with an antibody that is specific for α-helical middle pieces of non-secreted intermediate filament proteins that are characteristic of particular cells, wherein said antibody is selected from the group consisting of:

K,8–17.2, which is used for the identification of α-helical middle pieces or epitope-bearing fragments thereof which contain at least one monomer of cytokeratin 8;

K,18–27IV, which is used for identification of α-helical middle pieces or epitope-bearing fragments thereof which contain at least one monomer of cytokeratin 18;

K,8–9B1, which is used for identification of α-helical middle pieces or epitope-bearing fragments thereof which contain at least one monomer of cytokeratin 18;

K,8–19.2, which is used for identification of α-helical middle pieces or epitope-bearing fragments thereof which contain at least one monomer of cytokeratin 19;

K,pan 1–8, which is used for identification of α-helical middle pieces or epitope-bearing fragments thereof which contain at least one monomer of cytokeratin 1 to 8; and VIM 3B4, which is used for identification of α-helical middle pieces or epitope-bearing fragments thereof which contain at least one monomer of vimentin; and (c) detecting whether the antibody has bound to said separated soluble α-helical middle pieces, the binding of said antibody to said separated soluble α-helical middle pieces identifying the cellular origin of said non-secreted intermediate filament proteins, and thus the cellular origin of said tumor cells.

14. The method of claim 13, wherein said body fluid is selected from the group consisting of blood, blood serum, cerebrospinal fluid, urine, amniotic fluid, and puncture fluids.

15. A method for identifying the cellular origin of non-secreted intermediate filament protein material in a tissue sample or body fluid, comprising the steps of:

(a) separating soluble α-helical middle pieces of non-secreted intermediate filament proteins present in said tissue sample or body fluid by centrifugation;

(b) contacting the resulting separated soluble α-helical middle pieces with an antibody that is specific for α-helical middle pieces of non-secreted intermediate filament proteins of particular cell type, wherein said antibody is selected from the group consisting of:

K,8–17.2, which is used for the identification of α-helical middle pieces or epitope-bearing fragments thereof which contain at least one monomer of cytokeratin 8;

K,18–27IV, which is used for identification of α-helical middle pieces or epitope-bearing fragments thereof which contain at least one monomer of cytokeratin 18;

K,8–9B1, which is used for identification of α-helical middle pieces or epitope-bearing fragments thereof which contain at least one monomer of cytokeratin 18;

K,8–19.2, which is used for identification of α-helical middle pieces or epitope-bearing fragments thereof which contain at least one monomer of cytokeratin 19;

K,pan 1–8, which is used for identification of α-helical middle pieces or epitope-bearing fragments thereof which contain at least one monomer of cytokeratin 1 to 8; and VIM 3B4, which is used for identification of α-helical middle pieces or epitope-bearing fragments thereof which contain at least one monomer of vimentin; and (c) detecting whether said antibody has bound to the separated soluble α-helical middle pieces in step (b), wherein the binding of said antibody to said separated soluble α-helical middle pieces identifies the cellular origin of said non-secreted intermediate filament protein material.

16. The method of claim 15, wherein said antibody is detectably labeled.

17. The method of claim 16, wherein said detectable label is peroxidase.

18. The method of claim 15, wherein said intermediate filament proteins are selected from the group consisting of vimentin and cytokeratins.

19. The method of claim 15, wherein in step (c) said alpha-helical middle pieces are determined quantitatively using a purified alpha-helical middle pieces standard.

* * * * *